US012778914B2

(12) United States Patent
Zhang et al.

(10) Patent No.: US 12,778,914 B2
(45) Date of Patent: Nov. 3, 2026

(54) USE OF COMPOSITION OF ALCOHOL AND COOLING AGENT IN REGULATING SEXUAL FUNCTIONS, PROTECTING CARDIOVASCULAR AND CEREBROVASCULAR SYSTEMS, PROMOTING REGENERATION OF LIVER CELLS, PREVENTING AND/OR TREATING TUMORS, AND IMPROVING IMMUNITY AND SLEEP QUALITY

(71) Applicant: QINGHAI SPRING MEDICINAL RESOURCES TECHNOLOGY CO., LTD., Xining (CN)

(72) Inventors: Xuefeng Zhang, Xining (CN); Guoxia Ma, Xining (CN)

(73) Assignee: QINGHAI SPRING MEDICINAL RESOURCES TECHNOLOGY CO., LTD., Xining (CN)

( * ) Notice: Subject to any disclaimer, the term of this patent is extended or adjusted under 35 U.S.C. 154(b) by 379 days.

(21) Appl. No.: 18/565,673

(22) PCT Filed: Jan. 27, 2022

(86) PCT No.: PCT/CN2022/074407

§ 371 (c)(1),
(2) Date: Nov. 30, 2023

(87) PCT Pub. No.: WO2022/252663

PCT Pub. Date: Dec. 8, 2022

(65) Prior Publication Data

US 2024/0252453 A1 Aug. 1, 2024

(30) Foreign Application Priority Data

Jun. 2, 2021 (CN) ........................ 202110614624.2

(51) Int. Cl.

| | |
|---|---|
| *A61K 31/16* | (2006.01) |
| *A23L 33/10* | (2016.01) |
| *A23L 33/105* | (2016.01) |
| *A61K 9/00* | (2006.01) |
| *A61K 31/045* | (2006.01) |
| *A61K 31/075* | (2006.01) |
| *A61K 31/122* | (2006.01) |
| *A61K 31/19* | (2006.01) |
| *A61K 31/194* | (2006.01) |
| *A61K 31/20* | (2006.01) |
| *A61K 31/201* | (2006.01) |
| *A61K 31/22* | (2006.01) |
| *A61K 31/225* | (2006.01) |
| *A61K 31/265* | (2006.01) |
| *A61K 45/06* | (2006.01) |
| *A61P 1/16* | (2006.01) |
| *A61P 9/00* | (2006.01) |
| *A61P 15/00* | (2006.01) |
| *A61P 25/20* | (2006.01) |
| *A61P 35/00* | (2006.01) |
| *A61P 37/04* | (2006.01) |

(52) U.S. Cl.

CPC ............ *A61K 31/16* (2013.01); *A61K 9/0095* (2013.01); *A61K 31/075* (2013.01); *A61K 31/19* (2013.01); *A61K 31/194* (2013.01); *A61K 31/20* (2013.01); *A61K 31/22* (2013.01); *A61K 31/225* (2013.01); *A61K 31/265* (2013.01); *A61P 25/20* (2018.01)

(58) Field of Classification Search

None

See application file for complete search history.

(56) References Cited

FOREIGN PATENT DOCUMENTS

| | | | | | |
|---|---|---|---|---|---|
| CN | 106729187 A | * | 5/2017 | | ......... A61K 36/8994 |
| CN | 109022188 A | | 12/2018 | | |
| CN | 109022223 A | | 12/2018 | | |
| CN | 114225038 A | | 3/2022 | | |
| JP | 2021003005 A | * | 1/2021 | | |

OTHER PUBLICATIONS

Jin et al., Nature Reviews Drug Discovery | vol. 22 | Mar. 2023 | 213-234 (Year: 2023).*
CN 106729187 A_English_ Specification (Year: 2017).*
Claims CN106729187A_english translation (Year: 2017).*
Rachdaoui et al., Effects of Alcohol on the Endocrine System, Endocrinol Metab Clin North Am. Sep. 2013 ; 42(3): 593-615 (Year: 2013).*
Lopez-Lazaro, Miguel, A local mechanism by which alcohol consumption causes cancer, Oral Oncology 62 (2016) 149-152 (Year: 2016).*
JP2021003005A_English Translation (Year: 2021).*
English abstract for CN 109022188 A (2018).
English abstract for CN 109022223 A (2018).
English abstract for CN 114225038 A (2022).
Chen et al. (2006). Research Progress of Hepatic Neuroendocrine Compartment. World Chinese Journal of Digestology, 14(30), 2954-2957.

(Continued)

*Primary Examiner* — Kortney L. Klinkel
*Assistant Examiner* — Alison Azar Hastings
(74) *Attorney, Agent, or Firm* — Caesar Rivise, PC

(57) ABSTRACT

A use of a composition of alcohol and a cooling agent in regulating a sexual function, protecting a cardiovascular and cerebrovascular system, promoting hepatocyte regeneration, fighting against a tumor, and improving the immunity and sleep quality, relating to the fields of medicine, and health care products and food. The components of the composition comprise: alcohol and a cooling agent. Moreover, the composition comprises an organic acid. In the composition, the content of alcohol is 1-99% vol, and the content of the cooling agent is 0.05-500 ppm. The composition can regulate the sexual function, protect the cardiovascular and cerebrovascular system, promote the hepatocyte regeneration, fight against the tumor, and improve the immunity and sleep quality within a short period.

22 Claims, No Drawings

(56) References Cited

OTHER PUBLICATIONS

English abstract for Chen et al. (2006). Research Progress of Hepatic Neuroendocrine Compartment. World Chinese Journal of Digestology, 14(30), 2954-2957.
Gao et al. (1997). Control Function of Control Pathway of Parasympathetic Signaling System in vivo. Physiology of Human Information Control System: Modern Chinese Medicine Physiology and Pharmacology (Part I). Inner Mongolia People's Publishing House. pp. 370-373.
Kazadi et al. (2018). Gastric cooling and menthol cause an increase in cardiac parasympathetic efferent activity in healthy adult human volunteers. Experimental Physiology, 103(10), 1302-1308.
Zhu et al. (2015). Effect of regulating and balancing autonomic nerve. High Potential Hyperthermia. People's Military Medical Press, 36-38.
International Search Report from corresponding PCT/CN2022/074407 mailed Apr. 28, 2022.

* cited by examiner

USE OF COMPOSITION OF ALCOHOL AND COOLING AGENT IN REGULATING SEXUAL FUNCTIONS, PROTECTING CARDIOVASCULAR AND CEREBROVASCULAR SYSTEMS, PROMOTING REGENERATION OF LIVER CELLS, PREVENTING AND/OR TREATING TUMORS, AND IMPROVING IMMUNITY AND SLEEP QUALITY

CROSS-REFERENCE TO RELATED APPLICATIONS

This application is a U.S. National Phase Application of PCT/CN2022/074407, filed Jan. 27, 2022, which claims priority to CN 202110614624.2, filed Jun. 2, 2021, the contents of which applications are incorporated herein by reference in their entireties for all purposes.

TECHNICAL FIELD

The present invention belongs to the fields of medicine, health care and food, and specifically relates to use of a composition of alcohol and a cooling agent in regulating sexual functions, protecting cardiovascular and cerebrovascular systems, promoting regeneration of liver cells, preventing and/or treating tumors, and improving immunity and sleep quality.

BACKGROUND

Most people are busy at work, under great pressure, often drinking too much in social occasions, and lack of exercise. With the increasing pressure of life and work, their bodies are prone to long-term sympathetic nerve hyper tension. Sustained excessive excitement of sympathetic nerve will lead to many diseases, such as autoimmunity decline, sexual dysfunction, and poor sleep or insomnia.

Long-term excessive drinking will lead to cardiovascular and cerebrovascular diseases, alcoholic liver diseases (ALD) and tumors. In 2021, the International Agency for Research on Cancer (IARC) affiliated to the WHO issued a report on the global burden of alcohol-related cancers in Lancet Oncology. This report shows that in 2020, approximately 740,000 new cancers worldwide will be associated with alcohol drinking, including 76.7% in men and 23.3% in women. China's patients with cardiovascular and cerebrovascular diseases have exceeded 270 million people. Alcoholic liver disease (ALD) is a common clinical form of liver injury. The latest epidemiological surveys have found that ALD continues to be one of the common diseases that seriously jeopardize public health worldwide and is on the rise year after year. More than 90% of alcoholics are susceptible to fatty liver, 10%-35% develop alcoholic hepatitis, and about 8%-20% of chronic alcoholics evolve into cirrhosis of the liver, or even lead to liver cancer. In China, nearly 3 million people die from cardiovascular and cerebrovascular diseases each year, accounting for 51% of the total annual causes of death. However, 75% of survivors lost their ability to work to varying degrees, and 40% were severely disabled.

2018 China Sleep Quality Survey Report released by the Sleep and Breathing Center of Beijing Chaoyang Hospital surveyed 100,000 people, covering all provinces in China. Survey results show that 83.81% of respondents were often troubled by sleep problems. The survey shows that China's sleep problems are rising year by year, sleep problems are gradually transformed into a social problem, and people with sleep problems are often accompanied by autoimmunity decline, sexual dysfunction and other symptoms.

Most of people who have the above health problems such as weakened immunity, decreased sexual functions and poor sleep cannot be detected for actual disease and cannot be effectively treated by drugs for a long time. Generally, they are treated through diets or by administering health supplements, but those ways cannot be effective in short-term relief of weakened immunity, decreased sexual functions, poor sleep and other health problems. In addition, treatment through diets or administering health supplements takes a long time and is slow to take effect, so patients are difficult to persist in such treatment.

SUMMARY

The present invention provides use of a composition of alcohol and a cooling agent in regulating sexual functions, protecting cardiovascular and cerebrovascular systems, promoting regeneration of liver cells, preventing and/or treating tumors, and improving immunity and sleep quality.

Further, the alcohol in the composition is 1% vol-99% vol, and the cooling agent therein is 0.05 ppm-500 ppm.

Preferably, the alcohol in the composition is 30% vol-80% vol, and the cooling agent therein is 10 ppm-200 ppm.

More preferably, the alcohol in the composition is 30% vol-60% vol, and the cooling agent therein is 10 ppm-100 ppm.

Further, the cooling agent is a substance having the ability to activate a receptor of a thermoreceptor TRPM8. The cooling agent includes at least one of menthyl acetate, L-menthyl lactate, monomethyl succinate, L-monomenthyl glutarate, L-menthol ethylene glycol carbonate, L-menthol 1-(or 2-)-propylene glycol carbonate, 3-L-menthoxypropane-1,2-diol, 3-L-menthoxy-2-methylpropane-1,2-diol, N-ethyl-2-isopropyl-5-methylcyclohexane carboxamide, N,2,3-trimethyl-2-isopropylbutamide, menthol or menthone.

Further, the composition includes an organic acid.

Further, the organic acid is 150 ppm-30,000 ppm.

Further, the organic acid is 1,000 ppm-10,000 ppm.

Further, the organic acid is 1,000 ppm-6,000 ppm.

Further, the organic acid is selected from at least one of formic acid, acetic acid, propionic acid, lactic acid, butyric acid, butanedioic acid, pentanoic acid, hexanoic acid, heptanoic acid, octanoic acid, nonanoic acid, decanoic acid, citric acid, malic acid, tartaric acid, oxalic acid, oleic acid, linoleic acid, palmitic acid or lauric acid.

The beneficial effect of the present invention is that the cooling agent is added into a base liquor with a specific alcohol concentration, or cooling agent natural plants (such as peppermint and spearmint) including menthol are added into to take participate in all fermentation stages of various liquors to obtain the cooling agent, then the cooling agent and the alcohol are controlled through blending or purification to prepare the composition having the ability of regulating sexual functions, protecting cardiovascular and cerebrovascular systems, promoting regeneration of liver cells, preventing and/or treating tumors, and improving immunity and sleep quality. The composition of the present invention can play the role of regulating sexual functions, protecting cardiovascular and cerebrovascular systems, promoting regeneration of liver cells, preventing and/or treating tumors, and improving immunity and sleep quality within 5-7 days by activating a parasympathetic nerve signaling pathway, thereby largely resolving the problem that common dietary therapies and health supplements are not able to improve sexual function, immunity and sleep quality within a short period, and enabling the organism to be protected, recuperated and restored. Additional organic acids in the base liquor including the cooling agent have a better effect. The compositions of the present invention can be utilized in the fields of medicine, food and health care products.

DETAILED DESCRIPTION

Terminology "liquor" is distilled alcoholic drink, fermented alcoholic drink, alcoholic beverages or integrated alcoholic beverage.

The human body is a complex system, which maintains the balance of body functions through various adjustments, rather than a single adjustment. The present invention provides use of a composition of alcohol and a cooling agent in regulating sexual functions, protecting cardiovascular and cerebrovascular systems, promoting regeneration of liver cells, preventing and/or treating tumors, and improving immunity and sleep quality. The alcohol in the composition of the present invention is 1% vol-99% vol, and the cooling agent therein is 0.05 ppm-500 ppm. Preferably, the alcohol in the composition is 30% vol-80% vol, and the cooling agent therein is 10 ppm-200 ppm. More preferably, the alcohol in the composition is 30% vol-60% vol, and the cooling agent therein is 10 ppm-100 ppm.

The alcohol of the present invention is selected from at least one of distilled liquor, fermented liquor or edible alcohol.

The distilled liquor is selected from at least one of liquor, brandy, whiskey, vodka, rum, gin, tequila, or fruit distillate liquor.

The fermented liquor is selected from at least one of yellow liquor, beer, liquor, fruit liquor, fine rice liquor or milk liquor.

The cooling agent is a substance having the ability of activate a receptor of a thermoreceptor TRPM8, and includes at least one of menthyl acetate, L-menthyl lactate, monomethyl succinate, L-monomenthyl glutarate, L-menthol ethylene glycol carbonate, L-menthol 1-(or carbonate, 2-)-propylene glycol 3-L-menthoxypropane-1,2-diol, 3-L-menthoxy-2-methylpropane-1,2-diol, N-ethyl-2-isopropyl-5-methylcyclohexane carboxamide, N,2,3-trimethyl-2-isopropylbutamide, menthol or menthone.

Further, the applicant has found that the addition of organic acids to the base liquor including the cooling agent has a better effect in regulating sexual functions, protecting cardiovascular and cerebrovascular systems, promoting regeneration of liver cells, preventing and/or treating tumors, and improving immunity and sleep quality.

The organic acid is 150 ppm-30,000 ppm. Further, the organic acid is 1,000 ppm-10,000 ppm. Further, the organic acid is 1,000 ppm-6,000 ppm.

The organic acid is selected from at least one of formic acid, acetic acid, propionic acid, lactic acid, butyric acid, butanedioic acid, pentanoic acid, hexanoic acid, heptanoic acid, octanoic acid, nonanoic acid, decanoic acid, citric acid, malic acid, tartaric acid, oxalic acid, oleic acid, linoleic acid, palmitic acid or lauric acid.

The composition of the present invention also includes water to adjust alcohol concentration.

A method for preparing the composition of the present invention includes the following steps: dissolving the cooling agent in alcohol; then adding water and mixing the mixture well. Alternatively, dissolving the cooling agent in alcohol; then adding an organic acid; finally adding water and mixing the mixture well.

Test results show that healthy adults who drink a dose of alcohol, cooling agent or organic acid alone over a short period from 5 to 7 days have no significant effect in regulating sexual functions, protecting cardiovascular and cerebrovascular systems, promoting regeneration of liver cells, preventing and/or treating tumors, and improving immunity and sleep quality. Drinking a dose of a composition of a cooling agent and an organic acid or a dose of a composition of alcohol and an organic acid in a short period has no significant effect in regulating sexual functions, protecting cardiovascular and cerebrovascular systems, promoting regeneration of liver cells, preventing and/or treating tumors, and improving immunity and sleep quality. However, drinking a dose of a composition of alcohol and a cooling agent in a short period has an improvement effect in regulating sexual functions, protecting cardiovascular and cerebrovascular systems, promoting regeneration of liver cells, preventing and/or treating tumors, and improving immunity and sleep quality. Drinking a dose of a composition of alcohol, a cooling agent and an organic acid has a significant improvement effect in regulating sexual functions, protecting cardiovascular and cerebrovascular systems, promoting regeneration of liver cells, preventing and/or treating tumors, and improving immunity and sleep quality.

The composition in this application is used for regulating sexual functions, protecting cardiovascular and cerebrovascular systems, promoting regeneration of liver cells, preventing and/or treating tumors, and improving immunity and sleep quality, which is mainly related to the human body's intake of the alcohol and cooling agent in the composition. In view of the body's adaptation to taste and the body's tolerance to alcohol, the intake of the composition may depend on the content of alcohol and cooling agent in the composition. When the alcohol and the cooling agent in the composition are low, the intake of the composition can be increased to increase the intake of the alcohol and cooling agent, thereby playing the role of regulating sexual functions, protecting cardiovascular and cerebrovascular systems, promoting regeneration of liver cells, preventing and/or treating tumors, and improving immunity and sleep quality. When the alcohol and the cooling agent in the composition are high, the composition can be diluted with water to satisfy different body's requirements for the adaptation of taste and the tolerance of alcohol and achieve the effect of regulating sexual functions, protecting cardiovascular and cerebrovascular systems, promoting regeneration of liver cells, preventing and/or treating tumors, and improving immunity and sleep quality.

Table A shows a recommended intake range.

TABLE A

| Recommended intake range of composition | | | | | | |
|---|---|---|---|---|---|---|
| Alcohol % vol | Cooling agent ppm | Organic acid ppm | Composition intake mL | Pure alcohol intake mL | Cooling agent intake mg | Acid intake mg |
| 1-30 | 0.05-10 | 150-1000 | 50-1000 | 0.5-300 | 2.5 μg-10 | 7.5-1000 |
| 30-60 | 10-100 | 1000-6000 | 15-500 | 4.5-300 | 0.15-50 | 15-3000 |
| 60-80 | 100-200 | 6000-10000 | 15-250 | 9-200 | 1.5-50 | 90-2500 |
| 80-99 | 200-500 | 10000-30000 | 10-200 | 8-198 | 2-100 | 100-6000 |

Clinical studies have shown that long-term excessive intake of alcohol can lead to sleep and sexual dysfunction, and even can lead to the onset of cardiovascular disease and alcoholic liver disease, and even the development of tumors, which has the significant impact on the body's immune system. The inhibitory effect of alcohol on the central nervous system means the excitatory effect from cerebral cortex down through limbic system, cerebellum, reticulate structure and medulla oblongata with the dose increase. This is due to the fact that alcohol acts on the postsynaptic membrane γ-aminobutyric acid (GABA) receptor in the brain, thus inhibiting the inhibitory effect of GABA on the brain. As the concentration of the alcohol increases, it will further bind with other receptors, thereby causing a wide effect. Studies have shown that alcohol reduces immune function, inhibits interferon secretion, and interferes with the responsiveness of original antibodies to newly introduced antigens. Studies have shown that long-term heavy drinking can lead to sexual dysfunction in rats, which arises from the fact that alcohol inhibits the hypothalamic-pituitary-gonadal axes, lowering serum levels and directly inhibiting sexual function in rats. In addition, alcohol inhibition can further lead to penile smooth muscle atrophy, inhibiting the activity of choline acetyltransferase in penile tissues, thus indirectly inhibiting sexual function in rats.

Studies have shown that menthol derivatives can shorten sleep latency, antagonize the central excitatory effect of thiosemicarbazide, and improve sleep quality; at the same time, L-menthol and its derivatives can significantly inhibit the expression levels of glutamate receptors and acetylcholinesterase in the hippocampal region of the rat, thereby improving the cognitive ability and memory of the rat; in addition, studies also have shown that L-menthol and its derivatives have an antidepressant, anti-convulsion and hypnotic effect on the organism. Researchers have found that several menthol derivatives can activate TRPM8, and have higher efficacy and specificity than menthol, with great development potential. Studies show that TRPM8 activation can improve vascular tension and prevent hypertension. TRPM8 is widely distributed. In addition to TRPM8 expressed in prostate cancer, it is also expressed in some non-prostate primary tumors, and associated with the survival and growth of tumor cells; and it is likely to be a new target for anti-tumor therapy.

Organic acids can regulate a cellular immune system, induce host cells to produce antimicrobial peptides to achieve indirect bacterial inhibition, thereby providing body immunity. Meanwhile, studies have reported that succinic acid has a regulation effect on both GABA and Glu neurotransmitter systems in the CAI region of rat hippocampus, and it may act on the GABA system through the regulation mechanism that centers on calcium ions.

The present invention initially investigates the useful effect of the composition of the alcohol and the cooling agent in regulating sexual functions, protecting cardiovascular and cerebrovascular systems, promoting regeneration of liver cells, preventing and/or treating tumors, and improving immunity and sleep quality, and especially for the useful effect of the composition of the alcohol, the cooling agent and the organic acid in regulating sexual functions, protecting cardiovascular and cerebrovascular systems, promoting regeneration of liver cells, preventing and/or treating tumors, and improving immunity and sleep quality. According to the present invention, 3 items of immunoglobulin (IgA, IgG, IgM), serotonin (5-HT), estradiol ($E_2$), testosterone (T) and nitric oxide (NO) in blood are measured to evaluate the function of the composition in regulating sexual functions, protecting cardiovascular and cerebrovascular systems, promoting regeneration of liver cells, preventing and/or treating tumors, and improving immunity and sleep quality; however, for the male, interferon-γ (IFN-γ) needs to be measured; and for the female, progesterone (P), dopamine (DA), endorphin (β-EP) and the human deep sleep percentage are measured.

Immunoglobulin is a key substance of anti-infection in the body. It is critical to maintain a good level of immunoglobulin against viral and bacterial infections. Clinically, immunoglobulin IgA, IgG and IgM are often examined. Concentration of IgA, IgG and IgM represents the level of humoral immune function, and large concentration indicates strong humoral immune function.

Interferon-γ (IFN-γ) is a representative cytokine secreted by T lymphocytes, and has antiviral and immunoregulation effects in immune and inflammatory reaction, tumor prevention and inhibition of cell division. IFN-γ has become a widely concerned anti-tumor drug due to its anti-tumor cell proliferation, inhibition of tumor angiogenesis, and immunoregulation effects. IFN-γ can significantly inhibit the growth of a variety of tumors and has been applied to clinical trials. It helps the body immune system to recognize and kill tumor cells by increasing the expression levels of adhesion molecules and MHC molecules on the surfaces of tumor cells and antigen presenting cells and promotes the recruitment of more immune cells, thereby better exerting its anti-tumor effects. Studies have shown that in tumor microenvironment, IFN-γ not only activates CD4+Th1 cells to exert their immune function, but also inhibits proliferation of cancer cells, promotes apoptosis of cancerous cells, directly kills cancer cells and promotes the high expression level of major histocompatibility complex class-I molecules in cancer cells, so that they are recognized by specific T cells.

Serotonin (5-HT) is an important immunoregulation factor, which can promote the lethality of natural killer (NK)

cells associated with anti-tumor, anti-virus, etc., enhance phagocytosis of macrophages, and promote the proliferation and activation of T cells. As an amine neurotransmitter, serotonin is a natural mood stabilizer and important for us to gain happiness, emotional calm, and concentrated attention. At the same time, recent studies have found that 5-HT can also promote cell mitosis and participate in tissue remodeling. In recent years, many studies have found that 5-HT plays an important role in regulating the proliferation of hepatocytes during liver regeneration. Platelets are the main carriers of 5-HT in blood and can transport 5-HT to various organs.

Estradiol is an estrogen, and high estradiol can inhibit the synthesis and secretion of androgens by testis, which leads to sexual dysfunction due to insufficient secretion of androgen. Estrogen maintains thickness and elasticity of vaginal mucosa and vaginal lubrication in the stage of sexual arousal.

Androgens and estrogens are important for the development, functional maintenance, metabolism, and aging of the male and female reproductive organs. Maintaining a high ratio of testosterone/estradiol ($T/E_2$) in the male body is of great significance for maintaining erectile function, sperm formation, and fertilization ability. Female sexual desire is primarily determined by testosterone (T), and testosterone supplement can increase female sexual desire and good mood. When the testosterone/estradiol (T/E2) ratio is increased, testosterone is a highly effective aphrodisiac for women.

Nitric oxide (NO) is a serum indicator related to erectile function, which can relax cavernous vascular smooth muscle and cause erection. It is a key substance to ensure male erectile function. Nitric oxide can increase the blood flow of genitals and play an important role in maintaining normal sexual function. It can cause hyperaemia of clitoris and vagina, increase clitoris sensitivity and vagina lubricity. Meanwhile, it is also closely related to the cardiovascular and cerebrovascular systems. Endothelium-derived relaxing factor (EDRF) first discovered in 1980 has now been confirmed to be NO, which has a vasodilation effect and plays a role as a messenger for intracellular and intercellular transmission of biological information in pathological conditions such as ischemia. Studies have shown that nitric oxide contacts and relaxes smooth muscle cells in arteries, dilating the arteries, which results in decreased hypertension and improves blood flow. In addition, nitric oxide prevents blood from clotting in some dangerous areas. If blood coagulates in the heart or brain, the patient suffers from heart disease or stroke. Provided that the body produces a sufficient amount of nitric oxide, the risk of the heart disease is greatly reduced. Therefore nitric oxide can effectively lower blood pressure and prevent the stroke and the heart disease.

Progesterone increases female sexual desire and dopamine increases sexual desire and arousal.

Serum endorphin (β-EP) is a very important neuroregulator substance in the body and known as the body's natural opium and the "pleasure hormone". It can help people to maintain a young and happy state. At the same time, it can regulate a female endocrine system, relieve depression and enhance pleasure.

Sleep is extremely important for the protection of human health and the maintenance of normal physiological and psychological activities, and quality sleep also plays a greater role in protecting the body's immune function.

A large number of studies have shown that a parasympathetic nervous system plays an important regulation role in nervous, endocrine and immune systems, and its basic functions include: promoting secretion of digestive glands to increase secretions of salivary glands, stomach and intestine, liver and gall and pancreas and enhance gastrointestinal peristalsis; promoting the absorption of nutrients and energy; promoting secretion of insulin by pancreatic islet cells; promoting generation of hepatic glycogens to strengthen energy reserve; narrowing pupils to reduce stimulus; slowing down heartbeats, lowering blood pressure and the like to save the unnecessary consumption; participating in endocrine regulation and assisting in reproductive activities to cause dilation and erection of blood vessels of reproductive organs and increased secretion of sexual organs. Studies have also shown that parasympathetic nerve impulse can directly cause male erection. To sum up, a parasympathetic nerve helps our bodies to relax, allowing us to perceive peace and tranquility, pleasure and relaxation, thus enhancing energy reserves and fatigue recovery to achieve the recuperation, recovery and protection of the body. In addition, this can make a sympathetic nerve continually overexcited restore its normalcy and improve the chronic stress state of the body.

When the parasympathetic nerve is stimulated, it releases a large amount of acetylcholine (Ach) as a transmitter of nerve signals; and the acetylcholine is transmitted to a target organ through the parasympathetic nerve. An M receptor is short for muscarinicreceptor and widely found on effector cells innervated by parasympathetic postganglionic fibers. The M receptor receives signals (acetylcholine) from the parasympathetic nerve and produces a series of biochemical reactions within the cell, exhibiting the excitatory effect on a sympathetic nerve ending. In contrast, the M receptor achieves the excitatory effects of the parasympathetic nerve through a PLC/PIP2/IP3 signaling pathway.

An intracellular M receptor is linked to G protein, and a Gaq protein-linked receptor-mediated phospholipase C (PLC) signaling system is a widespread signal transduction mechanism. After activation of Gaq protein, PLCB is activated, then phosphatidylinositol-4,5-bisphosphate (PIP2) on cytomembrane is hydrolyzed into two secondary messengers, that is, inositol triphosphate (IP3) and diacylglycerol pyrophosphate (DAG). An M3 receptor is widely found in the endoplasmic reticulum membrane and serves as a channel protein capable of triggering intracellular calcium mobilization. It can bind with IP3 and trigger the intracellular calcium mobilization, leading to an increase in the intracellular calcium level, which initiates an intracellular calcium signaling system; in addition, a series of physiological processes, for example, ion channel function, cell cycle, glandular secretion, smooth muscle contraction, vasodilatation, and genital erection, are regulated through the change of enzymatic activity such as calmodulin of calcium ions. Therefore, the M3 receptor achieves the parasympathetic excitatory effect through the PLC/PIP2/IP3 signaling pathway.

Through experiments, it is found that the composition of the present invention can increase the expression level of the muscarinic acetylcholine receptor (M3 receptor) and the content of PLC and IP3 in the PLC/PIP2/IP3 signaling pathway. This indicates that the functions of the composition to regulate sexual functions, protect cardiovascular and cerebrovascular systems, promote regeneration of liver cells, prevent tumors, and improve immunity and sleep quality are regulated through the parasympathetic nerve signaling pathway.

The following will further explain embodiments of the present invention through specific embodiments, but does not indicate that the scope of protection of the present invention is limited in the scope described in the embodiments.

Example 1 Preparation of Composition 1 of the Present Invention

Composition 1 includes ingredients: cooling agent prepared by menthyl acetate, L-menthyl lactate, and monomethyl succinate by a weight ratio of 4:5:1; organic acid prepared by acetic acid, lactic acid, propionic acid, butyric acid, and hexanoic acid by a weight ratio of 14:15:1.5:1:1; and 4.5% vol beer as base liquor.

Composition 1 of alcohol is 1% vol, cooling agent is 0.05 ppm, and organic acid is 150 ppm was prepared with above cooling agent, organic acid, base liquor blended with purified water.

Example 2 Preparation of Composition 2 of the Present Invention

Composition 2 includes ingredients: cooling agent prepared by monomethyl succinate, L-monomenthyl glutarate, and N-ethyl-2-isopropyl-5-methylcyclohexane carboxamide by a weight ratio of 2:5:3; organic acid prepared by acetic acid, lactic acid, propionic acid, butanedioic acid, pentanoic acid, and heptanoic acid by a weight ratio of 7:8:1:2:1:1; and 40% vol whiskey as base liquor.

Composition 2 of alcohol is 30% vol, cooling agent is 10 ppm, and organic acid is 1000 ppm was prepared with above cooling agent, organic acid, base liquor blended with purified water.

Example 3 Preparation of Composition 3 of the Present Invention

Composition 3 includes ingredients: cooling agent prepared by N,2,3-trimethyl-2-isopropylbutamide, L-menthyl lactate, monomethyl succinate, and L-menthol ethylene glycol carbonate by a weight ratio of 2:3:2:3; organic acid prepared by formic acid, acetic acid, lactic acid, propionic acid, octanoic acid, nonanoic acid, and decanoic acid by a weight ratio of 1:8:5:2:1:1:1; and 60% vol Chinese Baijiu as a base liquor.

Composition 3 of alcohol is 60% vol, cooling agent is 100 ppm, and organic acid is 6000 ppm was prepared with above cooling agent, organic acid blended with base liquor.

Example 4 Preparation of Composition 4 of the Present Invention

Composition 4 includes ingredients: cooling agent prepared by monomethyl succinate, L-monomenthyl glutarate and N-ethyl-2-isopropyl-5-methylcyclohexane carboxamide by a weight ratio of 3:4:3; organic acid prepared by acetic acid, lactic acid, propionic acid, citric acid, malic acid and tartaric acid by a weight ratio of 5:5:1:2:1:1; and 12% vol Chinese rice liquor as base liquor.

Composition 4 of alcohol is 80% vol, cooling agent is 200 ppm, and organic acid is 10000 ppm was prepared with above cooling agent, organic acid base liquor blended with edible alcohol.

Example 5 Preparation of Composition 5 of the Present Invention

Composition 5 includes ingredients: cooling agent prepared by N,2,3-trimethyl-2-isopropylbutamide, L-menthyl lactate, 3-L-menthoxypropane-1,2-diol, L-menthol 1-(or 2-)-propylene glycol carbonate, and L-monomenthyl glutarate by a weight ratio of 4:1:2:3:1; organic acid prepared by lactic acid, propionic acid, hexanoic acid, citric acid and malic acid by a weight ratio of 5:1:1:2:2; and 99% vol dehydrated edible alcohol as a base liquor.

Composition 5 of alcohol is 99% vol, cooling agent is 500 ppm, and organic acid is 30000 ppm was prepared with above cooling agent, organic acid blended with base liquor.

Example 6 Preparation of Composition 6 of the Present Invention

Composition 6 includes ingredients: cooling agent prepared by menthyl acetate, L-menthyl lactate, and N,2,3-trimethyl-2-isopropylbutamide by a weight ratio of 2:3:5; organic acid prepared by acetic acid, butanedioic acid, hexanoic acid, citric acid and malic acid by a weight ratio of 3:1:1:4:2; and 50% vol Chinese Baijiu as a base liquor.

Composition 6 of alcohol is 50% vol, cooling agent is 50 ppm, and organic acid is 3000 ppm was prepared with above cooling agent, organic acid blended with base liquor.

Example 7 Preparation of Composition 7 of the Present Invention

Composition 7 includes ingredients: 150 ppm cooling agent prepared by L-menthyl lactate and monomethyl succinate by a weight ratio of 4:6; organic acid prepared by acetic acid, lactic acid, butanedioic acid, hexanoic acid and tartaric acid by a weight ratio of 3:3:1:1:2; and 70% vol edible alcohol as a base liquor.

Composition 7 of alcohol is 70% vol, cooling agent is 150 ppm, and organic acid is 8000 ppm was prepared with above cooling agent, organic acid blended with base liquor.

Comparative Example 1 Preparation of Low-Alcohol Composition 8

Composition 8 includes ingredients: cooling agent prepared by menthyl acetate, L-menthyl lactate and monomethyl succinate by a weight ratio of 4:5:1; organic acid prepared by acetic acid, lactic acid, propionic acid, butyric acid and hexanoic acid by a weight ratio of 14:15:1.5:1:1; and 15% vol sake as base liquor.

Composition 8 of alcohol is 0.5% vol, cooling agent is 5 ppm, and organic acid is 500 ppm was prepared with above cooling agent, organic acid, base liquor blended with purified water.

Comparative Example 2 Preparation of Low-Cooling Agent Composition 9

Composition 9 includes ingredients: cooling agent prepared by monomethyl succinate, L-monomenthyl glutarate, and N-ethyl-2-isopropyl-5-methylcyclohexane carboxamide by a weight ratio of 2:5:3; organic acid prepared by acetic acid, lactic acid, propionic acid, butanedioic acid, pentanoic acid and heptanoic acid by a weight ratio of 7:8:1:2:1:1; and 53% vol jiangxiangxing baijiu as a base liquor.

Composition 9 of alcohol is 53% vol, cooling agent is 0.04 ppm, and organic acid is 2000 ppm was prepared with above cooling agent, organic acid blended with base liquor.

Example 8 Preparation of Low-Acidity Composition 10

Composition 10 includes ingredients: cooling agent prepared by N,2,3-trimethyl-2-isopropylbutamide, L-menthyl lactate, monomethyl succinate and L-menthol ethylene glycol carbonate by a weight ratio of 2:3:2:3; organic acid prepared by formic acid, acetic acid, lactic acid, propionic acid, octanoic acid, nonanoic acid and decanoic acid by a weight ratio of 1:8:5:2:1:1:1; and 50% vol edible alcohol as a base liquor.

Composition 10 of alcohol is 50% vol, cooling agent is 50 ppm, and organic acid is 100 ppm was prepared with above cooling agent, organic acid blended with base liquor.

Comparative Example 3 Preparation of Alcohol-Free Composition 11

Composition 11 includes ingredients: cooling agent prepared by N,2,3-trimethyl-2-isopropylbutamide, L-monomenthyl glutarate, monomethyl succinate, and L-menthol ethylene glycol carbonate by a weight ratio of 2:3:3:1; organic acid prepared by acetic acid, lactic acid, propionic acid, citric acid, malic acid and tartaric acid by a weight ratio of 5:5:1:2:1:1.

Composition 11 of cooling agent is 5 ppm, and organic acid is 1000 ppm was prepared with above cooling agent, organic acid blended with purified water.

Comparative Example 4 Preparation of Cooling Agent-Free Composition 12

Composition 12 includes ingredients: organic acid prepared by acetic acid, butanedioic acid, hexanoic acid, citric acid and malic acid by a weight ratio of 3:1:1:4:2; and 53% vol jiangxiangxing baijiu as a base liquor.

Composition 12 of alcohol is 53% vol and organic acid is 2000 ppm was prepared with above organic acid blended with base liquor.

Example 9 Preparation of Composition 13 without Organic Acid

Composition 13 includes ingredients: cooling agent prepared by N,2,3-trimethyl-2-isopropylbutamide, 3-L-menthoxypropane-1,2-diol, L-menthol 1-(or 2-)-propylene glycol carbonate and L-monomenthyl glutarate by a weight ratio of 4:1:2:3; and 60% vol edible alcohol as a base liquor.

Composition 13 of alcohol is 60% vol and cooling agent is 100 ppm was prepared with above cooling agent blended with base liquor.

Example 10 Preparation of Composition 14 without Organic Acid

Composition 14 includes ingredients: cooling agent prepared by menthyl acetate, monomethyl succinate, menthol and menthone by a weight ratio of 10:8:2:1; and 1% vol edible alcohol as a base liquor.

Composition 14 of alcohol is 1% vol and cooling agent is 0.05 ppm was prepared with above cooling agent blended with base liquor.

Example 11 Preparation of Composition 15 without Organic Acid

Composition 15 includes ingredients: cooling agent prepared by menthyl acetate, L-menthyl lactate, monomethyl succinate, L-monomenthyl glutarate, and L-menthol ethylene glycol carbonate by a weight ratio of 3:2:1:2:2; and 30% vol edible alcohol as a base liquor.

Composition 15 of alcohol is 30% vol and cooling agent is 10 ppm was prepared with above cooling agent blended with base liquor.

Example 12 Preparation of Composition 16 without Organic Acid

Composition 16 includes ingredients: cooling agent prepared by monomethyl succinate, 3-L-menthoxy-2-methylpropane-1,2-diol, N-ethyl-2-isopropyl-5-methylcyclohexane carboxamide and 2-isopropyl-N-2,3-trimethylbutyramide by a weight ratio of 2:1:3:1; and 99% vol edible alcohol as a base liquor.

Composition 16 of alcohol is 99% vol and cooling agent is 500 ppm was prepared with above cooling agent blended with base liquor.

Amounts of alcohols, cooling agents and organic acids in the above compositions are shown in Table B.

TABLE B

Amounts of alcohols, cooling agents and organic acids in different compositions

| Composition | Alcohol/% vol | Cooling agent/ppm | Organic acid/ppm |
|---|---|---|---|
| 1 | 1 | 0.05 | 150 |
| 2 | 30 | 10 | 1000 |
| 3 | 60 | 100 | 6000 |
| 4 | 80 | 200 | 10000 |
| 5 | 99 | 500 | 30000 |
| 6 | 50 | 50 | 3000 |
| 7 | 70 | 150 | 8000 |
| 8 | 0.5 | 5 | 500 |
| 9 | 53 | 0.04 | 2000 |
| 10 | 50 | 50 | 100 |
| 11 | — | 5 | 1000 |
| 12 | 53 | — | 2000 |
| 13 | 60 | 100 | — |
| 14 | 1 | 0.05 | — |
| 15 | 30 | 10 | — |
| 16 | 99 | 500 | — |

Effect Verification

Sexual functions, cardiovascular and cerebrovascular systems, regeneration of liver cells, tumor prevention, immune and sleep quality improvement are evaluated for the indicators of the compositions prepared in the examples and comparative examples. Specific methods were as follows:

Subjects: 31 healthy males (19-56 years old) and 36 healthy females (25-50 years old). Participants were uniformly admitted to the study after fully understanding study liquor samples and study testing methods and requirements, and signing an informed consent form.

Drinking amount and time: 50 mL/person/day, with unified drinking at dinner for 7 consecutive days. Other alcoholic and functional beverages and health supplements are stopped drinking from first 7 days before drinking until various indicators are tested at the end of drinking. A before-and-after control comparison method was used.

Study Indicators

Serological indicators: blood was collected before drinking and 7 days after drinking, and 3 items of immunoglobulin (IgA, IgG, IgM), interferon-γ (IFN-γ), serotonin (5-HT), estradiol ($E_2$), testosterone (T), and nitric oxide (NO) were tested for the male. 3 items of serum immunoglobulin (IgA, IgG, IgM), serotonin (5-HT), estradiol ($E_2$), testosterone (T), progesterone (P), nitric oxide (NO), dopamine (DA), and endorphin (β-EP) were tested for the female.

Blood sample test organization: Chengdu Lilai Biotechnology Co., Ltd.

Sleep bracelet and scale assessment: a sleep monitoring bracelet (Huawei Bracelet 4) monitored daily sleep data from two days before drinking to two days after drinking. The purpose of monitoring two days before drinking was to obtain the average data of 2 days and avoid abnormal data or incomplete records of the bracelet.

Statistical methods: software SPSS 22.0, paired-samples T test.

Serum immunoglobulin indicators of men who drank the compositions prepared in the examples and the comparative examples were tested according to the above test methods, and results shown in Table 1 below were obtained.

TABLE 1

Changes in immunoglobulin before and after men drink the compositions

| Composition sample | Immunoglobulin indicators | Before drinking | After drinking | Increase/decrease % |
|---|---|---|---|---|
| Composition 1 | IgM (pg/mL) | 114.02 ± 38.52 | 134.22 ± 106.15 | 17.72 |
| | IgG (pg/mL) | 1.77 ± 0.67 | 1.96 ± 0.88 | 11.19 |
| | IgA (μg/mL) | 243.95 ± 76.24 | 264.47 ± 62.64 | 8.41 |
| Composition 2 | IgM (pg/mL) | 113.35 ± 35.62 | 135.72 ± 66.15 | 19.73 |
| | IgG (pg/mL) | 1.71 ± 0.54 | 1.94 ± 0.82 | 13.45 |
| | IgA (μg/mL) | 241.15 ± 66.24 | 265.97 ± 52.14 | 10.29 |
| Composition 3 | IgM (pg/mL) | 115.22 ± 34.26 | 136.02 ± 86.63 | 18.05 |
| | IgG (pg/mL) | 1.67 ± 0.81 | 1.91 ± 0.57 | 14.37 |
| | IgA (μg/mL) | 242.58 ± 56.85 | 266.74 ± 47.49 | 9.96 |
| Composition 4 | IgM (pg/mL) | 113.74 ± 36.32 | 134.22 ± 76.62 | 18.01 |
| | IgG (pg/mL) | 1.69 ± 0.68 | 1.95 ± 0.67 | 15.38 |
| | IgA (μg/mL) | 242.18 ± 64.27 | 265.97 ± 61.25 | 9.82 |
| Composition 5 | IgM (pg/mL) | 113.52 ± 35.28 | 133.82 ± 82.55 | 17.88 |
| | IgG (pg/mL) | 1.70 ± 0.69 | 1.91 ± 0.62 | 12.35 |
| | IgA (μg/mL) | 241.50 ± 67.04 | 265.19 ± 52.58 | 9.81 |
| Composition 6 | IgM (pg/mL) | 114.55 ± 35.12 | 135.17 ± 76.84 | 18.00 |
| | IgG (pg/mL) | 1.68 ± 0.73 | 1.97 ± 0.78 | 17.26 |
| | IgA (μg/mL) | 242.58 ± 70.29 | 265.29 ± 55.04 | 9.36 |
| Composition 7 | IgM (pg/mL) | 112.02 ± 31.53 | 133.96 ± 86.34 | 19.59 |
| | IgG (pg/mL) | 1.79 ± 0.75 | 1.99 ± 0.81 | 11.73 |
| | IgA (μg/mL) | 243.01 ± 70.11 | 266.38 ± 49.63 | 9.62 |
| Composition 8 | IgM (pg/mL) | 113.98 ± 38.52 | 114.12 ± 46.15 | 0.12 |
| | IgG (pg/mL) | 1.67 ± 0.82 | 1.65 ± 0.80 | −1.19 |
| | IgA (μg/mL) | 235.95 ± 76.74 | 240.47 ± 77.16 | −0.09 |
| Composition 9 | IgM (pg/mL) | 109.02 ± 38.52 | 109.92 ± 36.15 | 0.08 |
| | IgG (pg/mL) | 1.85 ± 0.91 | 1.87 ± 0.68 | 1.08 |
| | IgA (μg/mL) | 223.95 ± 76.34 | 224.47 ± 62.64 | 0.23 |
| Composition 10 | IgM (pg/mL) | 110.02 ± 38.52 | 122.27 ± 56.15 | 11.13 |
| | IgG (pg/mL) | 1.82 ± 0.58 | 1.94 ± 0.78 | 6.59 |
| | IgA (μg/mL) | 253.95 ± 92.54 | 269.47 ± 93.04 | 6.11 |
| Composition 11 | IgM (pg/mL) | 171.38 ± 58.12 | 173.64 ± 65.54 | 1.32 |
| | IgG (pg/mL) | 1.87 ± 0.92 | 1.86 ± 0.95 | −0.53 |
| | IgA (μg/mL) | 218.25 ± 98.18 | 217.93 ± 107.91 | −0.15 |
| Composition 12 | IgM (pg/mL) | 103.22 ± 29.48 | 102.92 ± 38.59 | −0.29 |
| | IgG (pg/mL) | 1.84 ± 0.81 | 1.86 ± 0.72 | 1.09 |
| | IgA (μg/mL) | 241.59 ± 80.45 | 242.74 ± 90.48 | 0.48 |
| Composition 13 | IgM (pg/mL) | 180.53 ± 50.12 | 192.26 ± 69.18 | 6.50 |
| | IgG (pg/mL) | 1.77 ± 0.67 | 1.86 ± 0.70 | 5.08 |
| | IgA (μg/mL) | 243.55 ± 81.45 | 255.42 ± 89.40 | 4.87 |
| Composition 14 | IgM (pg/mL) | 128.21 ± 41.37 | 133.59 ± 53.80 | 4.20 |
| | IgG (pg/mL) | 1.69 ± 0.61 | 1.76 ± 0.69 | 4.14 |
| | IgA (μg/mL) | 221.85 ± 60.24 | 230.23 ± 76.03 | 3.78 |
| Composition 15 | IgM (pg/mL) | 145.71 ± 46.11 | 159.29 ± 59.60 | 9.32 |
| | IgG (pg/mL) | 1.75 ± 0.52 | 1.85 ± 0.61 | 5.71 |
| | IgA (μg/mL) | 250.01 ± 72.06 | 264.18 ± 76.04 | 5.67 |
| Composition 16 | IgM (pg/mL) | 130.09 ± 50.18 | 147.24 ± 59.64 | 13.18 |
| | IgG (pg/mL) | 1.70 ± 0.49 | 1.83 ± 0.61 | 7.65 |
| | IgA (μg/mL) | 230.08 ± 75.14 | 246.41 ± 99.01 | 7.10 |

According to the above study results, it is found that for test groups drinking the compositions in the examples, their immunoglobulin levels increased to a varying extent, and low-acidity compositions 10 and compositions 13-16 without organic acids also slightly increased, but their percentage increase was inferior to that of the compositions 1-7. However, there were no significant differences in immunoglobulin levels before and after the alcohol-free composition, the low-alcohol composition, the cooling agent-free composition and the low-cooling agent composition in the comparative examples were drunk. It is proved that the compositions of the present invention can increase the male immunoglobulin level, thereby indicating that the compositions can enhance the immunity by increasing the male immunoglobulin level.

Serum immunoglobulin indicators of women who drank the compositions prepared in the examples and the comparative examples were tested according to the above test methods, and results shown in Table 2 below were obtained.

TABLE 2

| Changes in immunoglobulin before and after women drink the compositions | | | | |
|---|---|---|---|---|
| Composition sample | Immunoglobulin indicators | Before drinking | After drinking | Increase/ decrease % |
| Composition 1 | IgM (pg/mL) | 104.02 ± 32.52 | 123.12 ± 83.45 | 18.36 |
| | IgG (pg/mL) | 1.66 ± 0.64 | 1.85 ± 0.65 | 11.45 |
| | IgA (μg/mL) | 233.15 ± 56.74 | 251.17 ± 52.61 | 7.73 |
| Composition 2 | IgM (pg/mL) | 110.51 ± 31.64 | 130.15 ± 16.45 | 17.77 |
| | IgG (pg/mL) | 1.72 ± 0.24 | 1.93 ± 0.67 | 12.21 |
| | IgA (μg/mL) | 240.95 ± 62.74 | 264.14 ± 50.36 | 9.62 |
| Composition 3 | IgM (pg/mL) | 112.42 ± 37.16 | 135.82 ± 75.13 | 20.81 |
| | IgG (pg/mL) | 1.69 ± 0.69 | 1.90 ± 0.52 | 12.43 |
| | IgA (μg/mL) | 241.88 ± 57.75 | 265.94 ± 49.38 | 9.95 |
| Composition 4 | IgM (pg/mL) | 111.94 ± 39.24 | 133.58 ± 66.61 | 19.33 |
| | IgG (pg/mL) | 1.65 ± 0.68 | 1.91 ± 0.57 | 15.76 |
| | IgA (μg/mL) | 241.18 ± 64.27 | 264.47 ± 60.15 | 9.66 |
| Composition 5 | IgM (pg/mL) | 112.51 ± 38.18 | 134.12 ± 71.26 | 19.21 |
| | IgG (pg/mL) | 1.79 ± 0.61 | 1.98 ± 0.69 | 10.61 |
| | IgA (μg/mL) | 240.21 ± 69.38 | 266.09 ± 51.52 | 10.77 |
| Composition 6 | IgM (pg/mL) | 117.26 ± 31.62 | 138.13 ± 70.24 | 17.80 |
| | IgG (pg/mL) | 1.69 ± 0.70 | 1.89 ± 0.61 | 11.83 |
| | IgA (μg/mL) | 240.98 ± 71.09 | 264.74 ± 65.74 | 9.86 |
| Composition 7 | IgM (pg/mL) | 111.95 ± 36.38 | 134.62 ± 76.15 | 20.25 |
| | IgG (pg/mL) | 1.70 ± 0.66 | 1.92 ± 0.72 | 12.94 |
| | IgA (μg/mL) | 242.38 ± 68.82 | 265.18 ± 79.46 | 9.41 |
| Composition 8 | IgM (pg/mL) | 111.98 ± 31.25 | 112.92 ± 41.75 | 0.84 |
| | IgG (pg/mL) | 1.69 ± 0.62 | 1.67 ± 0.78 | −1.18 |
| | IgA (μg/mL) | 229.25 ± 86.36 | 231.74 ± 68.45 | 1.09 |
| Composition 9 | IgM (pg/mL) | 110.20 ± 39.85 | 111.52 ± 38.54 | 1.20 |
| | IgG (pg/mL) | 1.75 ± 0.65 | 1.77 ± 0.85 | 1.14 |
| | IgA (μg/mL) | 222.45 ± 71.48 | 223.97 ± 61.34 | 0.68 |
| Composition 10 | IgM (pg/mL) | 116.52 ± 48.73 | 128.93 ± 56.25 | 10.65 |
| | IgG (pg/mL) | 1.79 ± 0.74 | 1.88 ± 0.86 | 5.03 |
| | IgA (μg/mL) | 243.65 ± 67.54 | 255.17 ± 67.04 | 4.73 |
| Composition 11 | IgM (pg/mL) | 170.82 ± 65.21 | 172.46 ± 75.46 | 0.96 |
| | IgG (pg/mL) | 1.67 ± 0.81 | 1.66 ± 0.79 | −0.60 |
| | IgA (μg/mL) | 213.95 ± 89.58 | 214.33 ± 99.01 | 0.18 |
| Composition 12 | IgM (pg/mL) | 115.22 ± 49.84 | 116.92 ± 42.98 | 1.47 |
| | IgG (pg/mL) | 1.74 ± 0.74 | 1.75 ± 0.69 | 0.57 |
| | IgA (μg/mL) | 250.84 ± 79.47 | 249.14 ± 90.88 | −0.68 |
| Composition 13 | IgM (pg/mL) | 111.03 ± 30.52 | 122.27 ± 59.05 | 10.12 |
| | IgG (pg/mL) | 1.87 ± 0.71 | 1.98 ± 0.79 | 5.88 |
| | IgA (μg/mL) | 230.11 ± 63.82 | 243.24 ± 78.05 | 5.71 |
| Composition 14 | IgM (pg/mL) | 119.35 ± 48.21 | 127.71 ± 51.50 | 7.00 |
| | IgG (pg/mL) | 1.78 ± 0.63 | 1.86 ± 0.68 | 4.49 |
| | IgA (μg/mL) | 241.52 ± 59.37 | 250.41 ± 81.53 | 3.68 |
| Composition 15 | IgM (pg/mL) | 129.30 ± 51.16 | 141.36 ± 62.54 | 9.33 |
| | IgG (pg/mL) | 1.80 ± 0.61 | 1.91 ± 0.70 | 6.11 |
| | IgA (μg/mL) | 223.46 ± 71.28 | 238.44 ± 80.24 | 6.70 |
| Composition 16 | IgM (pg/mL) | 134.32 ± 60.21 | 148.90 ± 65.15 | 10.85 |
| | IgG (pg/mL) | 1.83 ± 0.66 | 1.99 ± 0.81 | 8.74 |
| | IgA (μg/mL) | 209.45 ± 72.17 | 225.48 ± 80.31 | 7.65 |

According to the above study results, it is found that for test groups drinking the compositions in the examples, their immunoglobulin levels increased to a varying extent, and low-acidity compositions 10 and compositions 13-16 without organic acids also slightly increased, but their percentage increase was inferior to that of the compositions 1-7. However, there were no significant differences in immunoglobulin levels before and after the alcohol-free composition, the low-alcohol composition, the cooling agent-free composition and the low-cooling agent composition in the comparative examples were drunk. It is proved that the compositions of the present invention can increase the female immunoglobulin level, thereby indicating that the compositions can enhance the immunity by increasing the female immunoglobulin level.

Interferon-γ (IFN-γ) indicators of men who drank the compositions prepared in the examples and the comparative examples were tested according to the above test methods, and results shown in Table 3 below were obtained.

TABLE 3

| Changes in interferon-γ (IFN-γ) before and after men drink the compositions | | | |
|---|---|---|---|
| Composition sample | Before drinking | After drinking | Increase/ decrease % |
| Composition 1 | 37.49 ± 12.36 | 41.77 ± 23.11 | 11.41 |
| Composition 2 | 34.44 ± 10.37 | 39.47 ± 13.01 | 14.61 |
| Composition 3 | 35.59 ± 12.56 | 40.17 ± 16.21 | 12.87 |
| Composition 4 | 35.81 ± 10.16 | 38.72 ± 18.45 | 8.13 |
| Composition 5 | 36.42 ± 10.86 | 40.92 ± 17.35 | 12.36 |
| Composition 6 | 38.09 ± 11.97 | 42.37 ± 15.74 | 11.24 |
| Composition 7 | 38.74 ± 12.94 | 42.57 ± 16.63 | 9.88 |
| Composition 8 | 36.82 ± 11.46 | 36.97 ± 14.18 | 0.41 |
| Composition 9 | 36.14 ± 15.36 | 36.43 ± 15.64 | 0.80 |
| Composition 10 | 36.59 ± 14.75 | 39.12 ± 16.11 | 6.91 |
| Composition 11 | 39.82 ± 9.68 | 39.17 ± 11.77 | −1.63 |
| Composition 12 | 33.41 ± 10.63 | 33.43 ± 11.46 | 0.06 |
| Composition 13 | 37.25 ± 13.05 | 39.81 ± 12.89 | 6.87 |
| Composition 14 | 35.60 ± 10.21 | 37.59 ± 11.35 | 5.59 |

TABLE 3-continued

| Changes in interferon-γ (IFN-γ) before and after men drink the compositions | | | |
|---|---|---|---|
| Composition sample | Before drinking | After drinking | Increase/ decrease % |
| Composition 15 | 38.42 ± 11.07 | 40.93 ± 12.01 | 6.53 |
| Composition 16 | 36.31 ± 10.92 | 38.94 ± 11.91 | 7.24 |

According to the above study results, it is found that for test groups drinking the compositions in the examples, their IFN-γ levels increased, and low-acidity compositions 10 and compositions 13-16 without organic acids also slightly increased, but their percentage increase was inferior to that of the compositions 1-7. However, there were no significant differences in IFN-γ levels before and after the alcohol-free composition, the low-alcohol composition, the cooling agent-free composition and the low-cooling agent composition in the comparative examples were drunk. It is proved that the compositions of the present invention can increase the male IFN-γ level, thereby indicating that the compositions can prevent tumors and enhance the immunity by increasing the male IFN-γ level.

Serotonin (5-HT) indicators of men who drank the compositions prepared in the examples and the comparative examples were tested according to the above test methods, and results shown in Table 4 below were obtained.

TABLE 4

| Changes in serotonin (5-HT) (pg/mL) before and after men drink the compositions | | | |
|---|---|---|---|
| Composition sample | Before drinking | After drinking | Increase/ decrease % |
| Composition 1 | 1.07 ± 0.55 | 1.31 ± 0.66 | 22.43 |
| Composition 2 | 1.01 ± 0.45 | 1.25 ± 0.76 | 23.76 |
| Composition 3 | 1.03 ± 0.51 | 1.27 ± 0.48 | 23.30 |
| Composition 4 | 1.06 ± 0.47 | 1.34 ± 0.69 | 26.42 |
| Composition 5 | 1.08 ± 0.35 | 1.30 ± 0.71 | 20.37 |
| Composition 6 | 1.07 ± 0.42 | 1.35 ± 0.74 | 26.17 |
| Composition 7 | 1.05 ± 0.58 | 1.33 ± 0.72 | 26.67 |
| Composition 8 | 1.01 ± 0.41 | 1.00 ± 0.61 | −1.00 |
| Composition 9 | 1.09 ± 0.57 | 1.10 ± 0.57 | 0.92 |
| Composition 10 | 1.04 ± 0.52 | 1.18 ± 0.67 | 13.46 |
| Composition 11 | 1.10 ± 0.39 | 1.11 ± 0.50 | 1.00 |
| Composition 12 | 1.09 ± 0.62 | 1.08 ± 0.69 | −0.9 |
| Composition 13 | 1.08 ± 0.51 | 1.19 ± 0.59 | 10.19 |
| Composition 14 | 1.06 ± 0.60 | 1.14 ± 0.54 | 7.55 |
| Composition 15 | 1.01 ± 0.49 | 1.11 ± 0.51 | 9.91 |
| Composition 16 | 1.04 ± 0.53 | 1.17 ± 0.59 | 12.5 |

According to the above study results, it is found that for test groups drinking the compositions in the examples, their serotonin levels (5-HT) significantly increased, and low-acidity compositions 10 and compositions 13-16 without organic acids also slightly increased, but their percentage increase was inferior to that of the compositions 1-7. However, there were no significant differences in serotonin (5-HT) levels before and after the alcohol-free composition, the low-alcohol composition, the cooling agent-free composition and the low-cooling agent composition in the comparative examples were drunk. It is proved that the compositions of the present invention can increase the male serotonin (5-HT) level, thereby indicating that the compositions can promote the regeneration of liver cells and enhance the immunity by increasing the male 5-HT level.

Serotonin (5-HT) indicators of women who drank the compositions prepared in the examples and the comparative examples were tested according to the above test methods, and results shown in Table 5 below were obtained.

TABLE 5

| Changes in serotonin (5-HT) (pg/mL) before and after women drink the compositions | | | |
|---|---|---|---|
| Composition sample | Before drinking | After drinking | Increase/ decrease % |
| Composition 1 | 1.04 ± 0.45 | 1.23 ± 0.56 | 18.27 |
| Composition 2 | 1.02 ± 0.41 | 1.23 ± 0.59 | 20.59 |
| Composition 3 | 1.03 ± 0.48 | 1.25 ± 0.53 | 21.36 |
| Composition 4 | 1.05 ± 0.47 | 1.29 ± 0.57 | 22.86 |
| Composition 5 | 1.08 ± 0.42 | 1.34 ± 0.61 | 24.07 |
| Composition 6 | 1.06 ± 0.53 | 1.34 ± 0.64 | 26.41 |
| Composition 7 | 1.04 ± 0.54 | 1.32 ± 0.71 | 26.92 |
| Composition 8 | 1.03 ± 0.51 | 1.04 ± 0.65 | 0.97 |
| Composition 9 | 1.11 ± 0.61 | 1.10 ± 0.66 | −0.90 |
| Composition 10 | 1.04 ± 0.52 | 1.16 ± 0.58 | 11.54 |
| Composition 11 | 1.08 ± 0.52 | 1.09 ± 0.62 | 0.93 |
| Composition 12 | 1.01 ± 0.49 | 1.00 ± 0.46 | −0.99 |
| Composition 13 | 1.05 ± 0.44 | 1.18 ± 0.68 | 12.38 |
| Composition 14 | 1.04 ± 0.47 | 1.11 ± 0.53 | 6.73 |
| Composition 15 | 1.07 ± 0.50 | 1.19 ± 0.61 | 11.21 |
| Composition 16 | 1.09 ± 0.54 | 1.20 ± 0.66 | 11.93 |

According to the above study results, it is found that for test groups drinking the compositions in the examples, their serotonin levels (5-HT) significantly increased, and low-acidity compositions 10 and compositions 13-16 without organic acids also had slight increase, but their percentage increase was inferior to that of the compositions1-7. However, there were no significant differences in serotonin (5-HT) levels before and after the alcohol-free composition, the low-alcohol composition, the cooling agent-free composition and the low-cooling agent composition in the comparative examples were drunk. It is proved that the compositions of the present invention can increase the female serotonin (5-HT) level, thereby indicating that the compositions can prompt the regeneration of liver cells and enhance the immunity by increasing the female 5-HT level.

Estradiol ($E_2$) indicators of men who drank the compositions prepared in the examples and the comparative examples were tested according to the above test 10 methods, and results shown in Table 6 below were obtained.

TABLE 6

| Changes in estradiol ($E_2$) (pg/mL) before and after men drink the compositions | | | |
|---|---|---|---|
| Composition sample | Before drinking | After drinking | Increase/ decrease % |
| Composition 1 | 42.99 ± 31.21 | 38.68 ± 29.83 | −10.03 |
| Composition 2 | 41.39 ± 21.63 | 37.21 ± 25.37 | −10.10 |
| Composition 3 | 41.99 ± 26.61 | 37.18 ± 22.82 | −11.46 |
| Composition 4 | 40.54 ± 25.74 | 36.18 ± 23.74 | −10.75 |
| Composition 5 | 41.94 ± 26.36 | 37.88 ± 21.36 | −9.68 |
| Composition 6 | 42.19 ± 29.66 | 38.36 ± 29.83 | −9.08 |
| Composition 7 | 42.36 ± 28.47 | 37.98 ± 25.73 | −10.34 |
| Composition 8 | 40.19 ± 29.21 | 39.88 ± 26.97 | −0.77 |
| Composition 9 | 40.54 ± 24.65 | 40.78 ± 26.13 | 0.59 |
| Composition 10 | 41.37 ± 30.37 | 38.83 ± 28.43 | −6.14 |
| Composition 11 | 43.59 ± 19.12 | 44.01 ± 16.69 | 0.96 |
| Composition 12 | 41.24 ± 20.56 | 40.98 ± 22.31 | −0.63 |
| Composition 13 | 44.38 ± 20.18 | 42.23 ± 24.52 | −4.84 |
| Composition 14 | 40.12 ± 19.85 | 37.58 ± 20.01 | −6.33 |
| Composition 15 | 44.92 ± 21.72 | 41.23 ± 21.24 | −8.21 |
| Composition 16 | 42.21 ± 22.03 | 38.90 ± 20.02 | −7.84 |

According to the above study results, it is found that for test groups drinking the compositions in the examples, their estradiol ($E_2$) levels decreased, and low-acidity compositions 10 and compositions 13-16 without organic acids also slightly decreased, but their percentage decrease was inferior to that of the compositions 1-7. However, there were no significant differences in estradiol ($E_2$) levels before and after the alcohol-free composition, the low-alcohol composition, the cooling agent-free composition and the low-cooling agent composition in the comparative examples were drunk. It is proved that the compositions of the present invention can decrease the male estradiol ($E_2$) levels, thereby indicating that the compositions can regulate the sexual functions by decreasing the male $E_2$ levels.

Estradiol ($E_2$) indicators of women who drank the compositions prepared in the examples and the comparative examples were tested according to the above test methods, and results shown in Table 7 below were obtained.

TABLE 7

Changes in estradiol ($E_2$) (pg/mL) before and after women drink the compositions

| Composition sample | Before drinking | After drinking | Increase/decrease % |
|---|---|---|---|
| Composition 1 | 156.69 ± 38.87 | 175.23 ± 34.35 | 11.83 |
| Composition 2 | 130.48 ± 30.31 | 147.19 ± 33.93 | 12.81 |
| Composition 3 | 221.58 ± 55.02 | 252.49 ± 76.61 | 13.95 |
| Composition 4 | 182.18 ± 61.74 | 210.57 ± 56.24 | 15.58 |
| Composition 5 | 386.28 ± 81.38 | 442.81 ± 90.96 | 14.63 |
| Composition 6 | 218.36 ± 76.83 | 252.63 ± 88.62 | 15.69 |
| Composition 7 | 129.98 ± 65.13 | 149.36 ± 76.19 | 14.91 |
| Composition 8 | 254.28 ± 96.47 | 258.19 ± 87.21 | 1.54 |
| Composition 9 | 361.78 ± 126.13 | 356.54 ± 105.35 | −1.45 |
| Composition 10 | 270.23 ± 88.43 | 289.37 ± 91.51 | 7.83 |
| Composition 11 | 244.82 ± 101.45 | 245.91 ± 97.68 | 0.45 |
| Composition 12 | 361.78 ± 106.21 | 360.10 ± 101.55 | −0.46 |
| Composition 13 | 301.58 ± 81.49 | 322.03 ± 94.27 | 6.78 |
| Composition 14 | 261.35 ± 98.34 | 272.30 ± 81.15 | 4.19 |
| Composition 15 | 314.15 ± 91.58 | 339.18 ± 99.50 | 7.97 |
| Composition 16 | 297.82 ± 94.80 | 325.85 ± 97.33 | 9.41 |

According to the above study results, it is found that for test groups drinking the compositions in the examples, their estradiol ($E_2$) levels increased, and low-acidity compositions 10 and compositions 13-16 without organic acids also slightly increased, but their percentage decrease was inferior to that of the compositions 1-7. However, there were no significant differences in estradiol ($E_2$) levels before and after the alcohol-free composition, the low-alcohol composition, the cooling agent-free composition and the low-cooling agent composition in the comparative examples were drunk. It is proved that the compositions of the present invention can increase the female estradiol ($E_2$) levels, thereby indicating that the compositions can regulate the sexual functions by increasing the female $E_2$ levels.

Testosterone/estradiol ($T/E_2$) indicators of men who drank the compositions prepared in the examples and the comparative examples were tested according to the above test methods, and results shown in Table 8 below were obtained.

TABLE 8

Changes in testosterone/estradiol ($T/E_2$) before and after men drink the compositions

| Composition sample | Before drinking | After drinking | Increase/decrease % |
|---|---|---|---|
| Composition 1 | 0.025 ± 0.010 | 0.027 ± 0.013 | 12.00 |
| Composition 2 | 0.021 ± 0.011 | 0.023 ± 0.011 | 9.52 |
| Composition 3 | 0.023 ± 0.010 | 0.025 ± 0.012 | 8.69 |
| Composition 4 | 0.022 ± 0.011 | 0.024 ± 0.011 | 9.10 |
| Composition 5 | 0.025 ± 0.014 | 0.028 ± 0.011 | 12.00 |
| Composition 6 | 0.023 ± 0.013 | 0.025 ± 0.013 | 8.69 |
| Composition 7 | 0.026 ± 0.011 | 0.029 ± 0.012 | 11.54 |
| Composition 8 | 0.021 ± 0.012 | 0.021 ± 0.013 | 0.00 |
| Composition 9 | 0.028 ± 0.013 | 0.027 ± 0.011 | −3.57 |
| Composition 10 | 0.022 ± 0.011 | 0.023 ± 0.012 | 4.35 |
| Composition 11 | 0.029 ± 0.015 | 0.028 ± 0.014 | −3.45 |
| Composition 12 | 0.026 ± 0.013 | 0.026 ± 0.015 | 0.00 |
| Composition 13 | 0.026 ± 0.014 | 0.028 ± 0.016 | 7.69 |
| Composition 14 | 0.025 ± 0.012 | 0.026 ± 0.014 | 4.00 |
| Composition 15 | 0.031 ± 0.015 | 0.033 ± 0.018 | 6.45 |
| Composition 16 | 0.027 ± 0.013 | 0.029 ± 0.015 | 7.41 |

According to the above study results, it is found that for test groups drinking the compositions in the examples, the ratio of testosterone/estradiol ($T/E_2$) increased, and low-acidity compositions 10 and compositions 13-16 without organic acids also slightly increased, but their percentage increase was inferior to that of the compositions 1-7. However, there was almost no increase in the ratio of testosterone/estradiol ($T/E_2$) before and after the alcohol-free composition, the low-alcohol composition, the cooling agent-free composition and the low-cooling agent composition in the comparative examples were drunk. It is proved that the compositions of the present invention can somewhat increase the ratio of testosterone/estradiol ($T/E_2$) for the male, thereby indicating that the compositions can regulate the sexual functions by increasing the ratio of testosterone/estradiol ($T/E_2$) for the male.

Testosterone/estradiol ($T/E_2$) indicators of women who drank the compositions prepared in the examples and the comparative examples were tested according to the above test methods, and results shown in Table 9 below were obtained.

TABLE 9

Changes in testosterone/estradiol ($T/E_2$) before and after women drink the compositions

| Composition sample | Before drinking | After drinking | Increase/decrease % |
|---|---|---|---|
| Composition 1 | 0.535 ± 0.179 | 0.587 ± 0.213 | 9.72 |
| Composition 2 | 0.421 ± 0.194 | 0.463 ± 0.208 | 12.59 |
| Composition 3 | 0.513 ± 0.210 | 0.572 ± 0.273 | 11.50 |
| Composition 4 | 0.322 ± 0.104 | 0.359 ± 0.175 | 11.49 |
| Composition 5 | 0.520 ± 0.214 | 0.589 ± 0.241 | 13.27 |
| Composition 6 | 0.603 ± 0.316 | 0.678 ± 0.364 | 12.44 |
| Composition 7 | 0.426 ± 0.201 | 0.482 ± 0.215 | 13.15 |
| Composition 8 | 0.521 ± 0.312 | 0.523 ± 0.341 | 0.38 |
| Composition 9 | 0.619 ± 0.415 | 0.617 ± 0.372 | −0.32 |
| Composition 10 | 0.622 ± 0.426 | 0.643 ± 0.358 | 3.38 |
| Composition 11 | 0.415 ± 0.201 | 0.420 ± 0.181 | 1.20 |
| Composition 12 | 0.619 ± 0.215 | 0.620 ± 0.271 | 0.16 |
| Composition 13 | 0.548 ± 0.247 | 0.569 ± 0.221 | 3.83 |
| Composition 14 | 0.574 ± 0.291 | 0.590 ± 0.285 | 2.79 |
| Composition 15 | 0.481 ± 0.214 | 0.499 ± 0.218 | 3.74 |
| Composition 16 | 0.632 ± 0.246 | 0.654 ± 0.301 | 3.48 |

According to the above study results, it is found that for test groups drinking the compositions in the examples, the ratio of testosterone/estradiol ($T/E_2$) increased, and low-acidity compositions 10 and compositions 13-16 without organic acids showed no slight increase. However, there was almost no increase in the ratio of testosterone/estradiol ($T/E_2$) before and after the alcohol-free composition, the low-alcohol composition, the cooling agent-free composition and the low-cooling agent composition in the comparative examples were drunk. It is proved that the compositions of the present invention can somewhat increase the ratio of testosterone/estradiol ($T/E_2$) for the female, thereby indicating that the compositions can regulate the sexual functions by increasing the ratio of testosterone/estradiol ($T/E_2$) for the female.

Nitric oxide (NO) indicators of men who drank the compositions prepared in the examples and the comparative examples were tested according to the above test methods, and results shown in Table 10 below were obtained.

TABLE 10

Changes in nitric oxide (NO) (mIU/mL) before and after men drink the compositions

| Composition sample | Before drinking | After drinking | Increase/ decrease % |
|---|---|---|---|
| Composition 1 | 11.17 ± 3.78 | 17.75 ± 3.72 | 58.91 |
| Composition 2 | 10.75 ± 2.45 | 18.18 ± 4.02 | 69.11 |
| Composition 3 | 10.36 ± 2.73 | 16.95 ± 3.64 | 63.61 |
| Composition 4 | 10.97 ± 2.85 | 17.23 ± 4.75 | 57.06 |
| Composition 5 | 10.35 ± 2.57 | 16.98 ± 4.12 | 64.06 |
| Composition 6 | 11.36 ± 2.58 | 18.85 ± 3.63 | 65.93 |
| Composition 7 | 10.77 ± 3.02 | 17.34 ± 5.72 | 61.00 |
| Composition 8 | 10.37 ± 2.68 | 10.45 ± 3.72 | 0.77 |
| Composition 9 | 11.18 ± 3.78 | 11.25 ± 3.23 | 0.63 |
| Composition 10 | 10.87 ± 3.38 | 14.45 ± 6.02 | 32.93 |
| Composition 11 | 11.30 ± 4.68 | 11.51 ± 4.12 | 1.86 |
| Composition 12 | 12.62 ± 4.78 | 12.52 ± 5.39 | −0.60 |
| Composition 13 | 12.45 ± 5.59 | 16.18 ± 6.02 | 29.96 |
| Composition 14 | 11.78 ± 4.85 | 14.45 ± 5.24 | 22.67 |
| Composition 15 | 13.01 ± 5.91 | 16.92 ± 7.05 | 30.06 |
| Composition 16 | 12.88 ± 6.15 | 17.02 ± 7.11 | 32.14 |

According to the above study results, it is found that for test groups drinking the compositions in the examples, their nitric oxide levels significantly increased, and low-acidity compositions 10 and compositions 13-16 without organic acids also slightly increased, but their percentage increase was inferior to that of the compositions 1-7. However, there was almost no increase in nitric oxide level before and after the alcohol-free composition, the low-alcohol composition, the cooling agent-free composition and the low-cooling agent composition in the comparative examples were drunk. It is proved that the compositions of the present invention can effectively increase the male nitric oxide level, thereby indicating that the compositions can regulate the sexual functions and protect the cardiovascular and cerebrovascular systems by increasing the male nitric oxide level.

Nitric oxide (NO) indicators of women who drank the compositions prepared in the examples and the comparative examples were tested according to the above test methods, and results shown in Table 11 below were obtained.

TABLE 11

Changes in nitric oxide (NO) (mIU/mL) before and after women drink the compositions

| Composition sample | Before drinking | After drinking | Increase/ decrease % |
|---|---|---|---|
| Composition 1 | 19.23 ± 16.14 | 27.63 ± 16.98 | 43.68 |
| Composition 2 | 17.75 ± 6.75 | 23.18 ± 5.92 | 30.59 |
| Composition 3 | 18.36 ± 6.23 | 26.95 ± 7.27 | 46.79 |
| Composition 4 | 16.37 ± 5.15 | 22.53 ± 8.75 | 37.63 |
| Composition 5 | 13.28 ± 6.73 | 19.48 ± 7.02 | 46.69 |
| Composition 6 | 12.16 ± 6.18 | 18.85 ± 5.83 | 55.02 |
| Composition 7 | 14.15 ± 8.07 | 19.84 ± 5.12 | 40.21 |
| Composition 8 | 11.37 ± 5.68 | 11.45 ± 5.25 | 0.70 |
| Composition 9 | 12.48 ± 6.08 | 12.55 ± 7.13 | 0.56 |
| Composition 10 | 13.27 ± 5.31 | 14.00 ± 4.18 | 5.50 |
| Composition 11 | 16.75 ± 6.08 | 16.52 ± 5.91 | −1.37 |
| Composition 12 | 15.48 ± 6.08 | 15.55 ± 6.70 | 0.45 |
| Composition 13 | 14.82 ± 5.68 | 15.40 ± 6.08 | 3.91 |
| Composition 14 | 18.70 ± 7.21 | 19.10 ± 8.85 | 2.14 |
| Composition 15 | 15.25 ± 6.03 | 16.09 ± 5.99 | 5.51 |
| Composition 16 | 16.56 ± 6.29 | 18.02 ± 7.54 | 8.81 |

According to the above study results, it is found that for test groups drinking the compositions in the examples, their nitric oxide levels significantly increased, and low-acidity compositions 10 and compositions 13-16 without organic acids showed no significant increase. However, there was almost no increase in nitric oxide level before and after the alcohol-free composition, the low-alcohol composition, the cooling agent-free composition and the low-cooling agent composition in the comparative examples were drunk. It is proved that the compositions of the present invention can effectively increase the female nitric oxide level, thereby indicating that the compositions can regulate the sexual functions and protect the cardiovascular and cerebrovascular systems by increasing the female nitric oxide level.

Progesterone (P) indicators of women who drank the compositions prepared in the examples and the comparative examples were tested according to the above test methods, and results shown in Table 12 below were obtained.

TABLE 12

Changes in progesterone (P) (ng/ml) before and after women drink the compositions

| Composition sample | Before drinking | After drinking | Increase/ decrease % |
|---|---|---|---|
| Composition 1 | 0.75 ± 0.35 | 0.94 ± 0.46 | 25.33 |
| Composition 2 | 1.20 ± 0.71 | 1.54 ± 0.84 | 28.33 |
| Composition 3 | 1.82 ± 0.85 | 2.35 ± 1.14 | 29.12 |
| Composition 4 | 0.95 ± 0.48 | 1.19 ± 0.65 | 25.26 |
| Composition 5 | 0.48 ± 0.21 | 0.63 ± 0.28 | 31.25 |
| Composition 6 | 1.30 ± 0.76 | 1.71 ± 0.92 | 31.54 |
| Composition 7 | 0.63 ± 0.36 | 0.85 ± 0.32 | 34.92 |
| Composition 8 | 1.44 ± 0.62 | 1.46 ± 0.77 | 1.39 |
| Composition 9 | 1.78 ± 0.64 | 1.77 ± 0.92 | −0.56 |
| Composition 10 | 0.85 ± 0.42 | 0.98 ± 0.55 | 15.29 |
| Composition 11 | 1.64 ± 0.71 | 1.66 ± 0.90 | 1.22 |
| Composition 12 | 1.58 ± 0.64 | 1.57 ± 0.92 | −0.63 |
| Composition 13 | 0.59 ± 0.29 | 0.68 ± 0.31 | 15.25 |
| Composition 14 | 0.55 ± 0.21 | 0.61 ± 0.28 | 10.91 |
| Composition 15 | 1.12 ± 0.43 | 1.28 ± 0.36 | 14.29 |
| Composition 16 | 1.48 ± 0.64 | 1.69 ± 0.49 | 14.19 |

According to the above study results, it is found that for test groups drinking the compositions in the examples, their progesterone (P) levels significantly increased, and low-acidity compositions 10 and compositions 13-16 without organic acids also slightly increased, but their percentage increase was inferior to that of the compositions 1-7. However, there was almost no increase in progesterone (P) level before and after the alcohol-free composition, the low-alcohol composition, the cooling agent-free composition and the low-cooling agent composition in the comparative examples were drunk. It is proved that the compositions of the present invention can effectively increase the female progesterone (P) level, thereby indicating that the compositions can regulate the sexual functions by increasing the female progesterone (P) level.

Dopamine (DA) indicators of women who drank the compositions prepared in the examples and the comparative examples were tested according to the above test methods, and results shown in Table 13 below were obtained.

TABLE 13

| Changes in dopamine (DA) (μmol/L) before and after women drink the compositions | | | |
|---|---|---|---|
| Composition sample | Before drinking | After drinking | Increase/ decrease % |
| Composition 1 | 0.61 ± 0.32 | 0.74 ± 0.41 | 21.31 |
| Composition 2 | 0.41 ± 0.20 | 0.51 ± 0.24 | 24.39 |
| Composition 3 | 0.70 ± 0.35 | 0.85 ± 0.44 | 21.43 |
| Composition 4 | 0.55 ± 0.38 | 0.69 ± 0.45 | 24.45 |
| Composition 5 | 0.48 ± 0.21 | 0.58 ± 0.26 | 20.83 |
| Composition 6 | 0.32 ± 0.16 | 0.41 ± 0.21 | 28.12 |
| Composition 7 | 0.63 ± 0.31 | 0.75 ± 0.42 | 19.05 |
| Composition 8 | 0.44 ± 0.22 | 0.43 ± 0.27 | −2.27 |
| Composition 9 | 0.74 ± 0.46 | 0.75 ± 0.52 | 1.35 |
| Composition 10 | 0.57 ± 0.26 | 0.65 ± 0.35 | 14.03 |
| Composition 11 | 0.51 ± 0.25 | 0.50 ± 0.20 | −1.96 |
| Composition 12 | 0.61 ± 0.28 | 0.62 ± 0.21 | 1.64 |
| Composition 13 | 0.59 ± 0.30 | 0.68 ± 0.41 | 15.25 |
| Composition 14 | 0.49 ± 0.22 | 0.54 ± 0.25 | 10.20 |
| Composition 15 | 0.61 ± 0.29 | 0.68 ± 0.38 | 11.47 |
| Composition 16 | 0.54 ± 0.25 | 0.59 ± 0.27 | 9.26 |

According to the above study results, it is found that for test groups drinking the compositions in the examples, their dopamine (DA) levels significantly increased, and low-acidity compositions 10 and compositions 13-16 without organic acids also increased, but their percentage increase was inferior to that of the compositions 1-7. However, there was almost no increase in dopamine (DA) level before and after the alcohol-free composition, the low-alcohol composition, the cooling agent-free composition and the low-cooling agent composition in the comparative examples were drunk. It is proved that the compositions of the present invention can effectively increase the female dopamine (DA) level, thereby indicating that the compositions can regulate the sexual functions by increasing the female dopamine (DA) level.

Endorphin (β-EP) indicators of women who drank the compositions prepared in the examples and the comparative examples were tested according to the above test methods, and results shown in Table 14 below were obtained.

TABLE 14

| Changes in endorphin (β-EP) (pg/mL) before and after women drink the compositions | | | |
|---|---|---|---|
| Composition sample | Before drinking | After drinking | Increase/ decrease % |
| Composition 1 | 166.61 ± 57.32 | 201.74 ± 76.41 | 21.08 |
| Composition 2 | 181.18 ± 67.12 | 221.25 ± 81.74 | 21.84 |
| Composition 3 | 202.26 ± 57.12 | 246.65 ± 78.82 | 21.94 |
| Composition 4 | 170.41 ± 61.62 | 214.63 ± 70.14 | 25.95 |
| Composition 5 | 160.64 ± 41.62 | 208.13 ± 45.18 | 29.56 |
| Composition 6 | 204.26 ± 57.12 | 258.47 ± 78.82 | 26.54 |
| Composition 7 | 192.74 ± 68.37 | 237.75 ± 46.31 | 23.35 |
| Composition 8 | 191.62 ± 68.37 | 190.75 ± 56.63 | −0.45 |

TABLE 14-continued

| Changes in endorphin (β-EP) (pg/mL) before and after women drink the compositions | | | |
|---|---|---|---|
| Composition sample | Before drinking | After drinking | Increase/ decrease % |
| Composition 9 | 174.47 ± 43.16 | 176.23 ± 47.86 | 1.01 |
| Composition 10 | 171.85 ± 50.46 | 196.38 ± 61.02 | 14.27 |
| Composition 11 | 195.37 ± 68.56 | 196.59 ± 72.66 | 0.62 |
| Composition 12 | 180.56 ± 53.75 | 179.32 ± 67.43 | −0.69 |
| Composition 13 | 169.61 ± 49.21 | 188.45 ± 60.20 | 11.11 |
| Composition 14 | 161.26 ± 30.64 | 176.27 ± 41.26 | 9.31 |
| Composition 15 | 185.19 ± 51.07 | 208.55 ± 57.21 | 12.61 |
| Composition 16 | 190.10 ± 70.24 | 216.81 ± 61.50 | 14.05 |

According to the above study results, it is found that for test groups drinking the compositions in the examples, their endorphin (β-EP) levels significantly increased, and low-acidity compositions 10 and compositions 13-16 without organic acids also increased, but their percentage increase was inferior to that of the compositions 1-7. However, there was almost no increase in endorphin (β-EP) level before and after the alcohol-free composition, the low-alcohol composition, the cooling agent-free composition and the low-cooling agent composition in the comparative examples were drunk. It is proved that the compositions of the present invention can effectively increase the female endorphin (β-EP) level, thereby indicating that the compositions can regulate the sexual functions by increasing the female ß-EP level.

The deep sleep percentages of persons who drank the compositions prepared in the examples and the comparative examples were tested according to the above test methods, and results shown in Table 15 below were obtained.

TABLE 15

| Changes in deep sleep percentage before and after persons drink the compositions | | | |
|---|---|---|---|
| Composition sample | Before drinking | After drinking | Increase/ decrease % |
| Composition 1 | 18.03 ± 3.48 | 21.70 ± 4.62 | 20.34 |
| Composition 2 | 18.57 ± 3.85 | 22.26 ± 3.91 | 19.87 |
| Composition 3 | 17.63 ± 3.36 | 21.16 ± 3.82 | 20.02 |
| Composition 4 | 18.23 ± 2.97 | 21.90 ± 4.25 | 20.13 |
| Composition 5 | 17.83 ± 2.86 | 20.99 ± 3.84 | 17.72 |
| Composition 6 | 17.68 ± 3.40 | 21.25 ± 3.80 | 20.19 |
| Composition 7 | 17.51 ± 3.18 | 21.18 ± 4.01 | 20.96 |
| Composition 8 | 17.36 ± 3.25 | 17.70 ± 4.42 | 1.96 |
| Composition 9 | 18.15 ± 3.12 | 18.01 ± 4.26 | −0.77 |
| Composition 10 | 17.57 ± 3.18 | 19.79 ± 3.63 | 12.64 |
| Composition 11 | 19.63 ± 5.51 | 19.57 ± 6.02 | −0.31 |
| Composition 12 | 16.99 ± 6.20 | 17.08 ± 5.37 | 0.53 |
| Composition 13 | 18.96 ± 6.73 | 21.59 ± 8.98 | 13.87 |
| Composition 14 | 17.00 ± 5.48 | 18.79 ± 6.03 | 10.53 |
| Composition 15 | 19.02 ± 8.05 | 21.27 ± 7.82 | 11.83 |
| Composition 16 | 18.25 ± 8.28 | 20.56 ± 9.43 | 12.66 |

According to the above study results, it is found that for test groups drinking the compositions in the examples, their deep sleep percentages increased to a varying extend, and low-acidity compositions 10 and compositions 13-16 without organic acids also increased, but their percentage increase was inferior to that of the compositions 1-7. However, there were no significant differences in deep sleep percentages before and after the alcohol-free composition, the low-alcohol composition, the cooling agent-free composition and the low-cooling agent composition in the comparative examples were drunk. It is proved that the compositions of the present invention can increase the human deep sleep percentage, thereby indicating that the compositions may improve the sleep quality by increasing the human deep sleep percentage.

It can be learned from the above data that the compositions of the present invention have the functions of regulating sexual functions, protecting cardiovascular and cerebrovascular systems, promoting regeneration of liver cells, preventing and/or treating tumors, and improving immunity and sleep quality, with the increased and lasting salivary secretion. Analysis on this phenomenon shows that the functions of the composition to regulate sexual functions, protect cardiovascular and cerebrovascular systems, promote regeneration of liver cells, prevent tumors, and improve immunity and sleep quality are regulated by activating the parasympathetic nerve signaling pathway. Therefore, the expression level of the M3 receptor and the content of the PLC and IP3 in the signaling pathway being tested can embody the activation of the parasympathetic nerve signaling pathway. The test method is as follows:

SPF male mice, after 7 days of acclimatization feeding, were randomized into groups of 10 mice each according to the randomized numerical expression. Blank control group: normal saline group; test group 1: composition 6; test group 2: 50% vol pure edible alcohol; test group 3: aqueous solution including 50 ppm cooling agent; test group 4: aqueous solution including 3000 ppm organic acid.

Administration method: a syringe sucked up the normal saline and the samples of each test group respectively at a dose of 15 mL/kg, and slowly dripped them into the oral cavity of the mice in small portions. The mice were administrated once a day for three consecutive days.

30 minutes after drug administration on the third day, mice were executed by spinal dislocation, and their submandibular gland tissues were homogenized in a homogenizer and centrifuged at 7000 r/min for 5 min, and the supernatant was taken. Enzyme-linked immunosorbent (ELISA) assay was used to determine M3, PLC and IP3. Results shown in Table 16 are obtained.

TABLE 16

M3, PLC and IP3 of submandibular gland tissue homogenates

| Test groups | M3 (pg/mL) | PLC (ng/mL) | IP3 (ng/mL) |
|---|---|---|---|
| Blank control group | 9.720 ± 0.579 | 7.020 ± 1.069 | 5.080 ± 0.530 |
| Test group 1 | 12.009 ± 0.651 | 12.975 ± 1.138 | 12.720 ± 1.320 |
| Test group 2 | 9.418 ± 0.674 | 6.498 ± 0.819 | 6.590 ± 0.946 |
| Test group 3 | 10.005 ± 0.548 | 7.273 ± 0.997 | 5.153 ± 1.103 |
| Test group 4 | 9.192 ± 0.523 | 7.938 ± 1.031 | 6.105 ± 0.862 |

According to the above study results, it is found that the test group 1 drinking the composition 6 had the expression level of M3, PLC and IP3 higher than the control group ($P<0.05$); there was no significant difference between test groups 2, 3, 4 only including alcohol, cooling agent or organic acid and the control group, indicating that the composition of the present invention can increase the expression level of the M3 receptor and activate the PLC/IP3 pathway of the parasympathetic nerve.

Through the above test results, it can be verified that the compositions of the present invention can play the role of regulating sexual functions, protecting cardiovascular systems, promoting regeneration of liver cells, preventing and/or treating tumors, and improving immunity and sleep quality by activating the parasympathetic nerve signaling pathway, and can be widely utilized in the fields of medicine, food and health care products.

The invention claimed is:

1. A method for regulating at least one physiological process of an individual, said method comprising administering to the individual at least one composition comprising at least one alcohol-containing potable, at least one cooling agent, and at least one organic acid, wherein the at least one composition is selected from the group consisting of:

(1) Composition 1 comprising 1% alcohol by volume, 0.05 ppm of the at least one cooling agent, 150 ppm of the at least one organic acid, and water, wherein:

the at least one cooling agent comprises menthyl acetate, L-menthyl lactate, and monomethyl succinate in a weight ratio of 4:5:1;

the at least one alcohol-containing potable comprises beer; and the at least one organic acid comprises acetic acid, lactic acid, propionic acid, butyric acid, and hexanoic acid in a weight ratio of 14:15:1.5:1:1;

(2) Composition 2 comprising 30% alcohol by volume, 10 ppm of the at least one cooling agent, 1000 ppm of the at least one organic acid, and water, wherein:

the at least one cooling agent comprises monomethyl succinate, L-monomenthyl glutarate, and N-ethyl-2-isopropyl-5-methylcyclohexane carboxamide in a weight ratio of 2:5:3;

the at least one alcohol-containing potable comprises whiskey; and the at least one organic acid comprises acetic acid, lactic acid, propionic acid, butanedioic acid, pentanoic acid, and heptanoic acid in a weight ratio of 7:8:1:2:1:1;

(3) Composition 3 comprising 60% alcohol by volume, 100 ppm of the at least one cooling agent, 6000 ppm of the at least one organic acid, and water, wherein:

the at least one cooling agent comprises N,2,3-trimethyl-2-isopropylbutamide, L-menthyl lactate, monomethyl succinate, and L-menthol ethylene glycol carbonate in a weight ratio of 2:3:2:3;

the at least one alcohol-containing potable comprises Baijiu; and the at least one organic acid comprises formic acid, acetic acid, lactic acid, propionic acid, octanoic acid, nonanoic acid, and decanoic acid in a weight ratio of 1:8:5:2:1:1:1;

(4) Composition 4 comprising 80% alcohol by volume, 200 ppm of the at least one cooling agent, 10,000 ppm of the at least one organic acid, and water, wherein:

the at least one cooling agent comprises monomethyl succinate, L-monomenthyl glutarate, and N-ethyl-2-isopropyl-5-methylcyclohexane carboxamide in a weight ratio of 3:4:3;

the at least one alcohol-containing potable comprises rice liquor and edible alcohol; and the at least one organic acid comprises acetic acid, lactic acid, propionic acid, citric acid, malic acid, and tartaric acid in a weight ratio of 5:5:1:2:1:1;

(5) Composition 5 comprising 99% alcohol by volume, 500 ppm of the at least one cooling agent, 30,000 ppm of the at least one organic acid, and water, wherein:

the at least one cooling agent comprises N,2,3-trimethyl-2-isopropylbutamide, L-menthyl lactate, 3-L-menthoxypropane-1,2-diol, L-menthol propylene glycol carbonate, and L-monomenthyl glutarate in a weight ratio of 4:1:2:3:1;

the at least one alcohol-containing potable comprises dehydrated ethanol; and the at least one organic acid comprises lactic acid, propionic acid, hexanoic acid, citric acid, and malic acid in a weight ratio of 5:1:1:2:2;

(6) Composition 6 comprising 50% alcohol by volume, 50 ppm of the at least one cooling agent, 3000 ppm of the at least one organic acid, and water, wherein:

the at least one cooling agent comprises menthyl acetate, L-menthyl lactate, and N,2,3-trimethyl-2-isopropylbutamide in a weight ratio of 2:3:5;

the at least one alcohol-containing potable comprises Baijiu; and the at least one organic acid comprises acetic acid, butanedioic acid, hexanoic acid, citric acid, and malic acid in a weight ratio of 3:1:1:4:2; and (7) Composition 7 comprising 70% alcohol by volume, 150 ppm of the at least one cooling agent, 8000 ppm of the at least one organic acid, and water, wherein:

the at least one cooling agent comprises L-menthyl lactate and monomethyl succinate in a weight ratio of 4:6;

the at least one alcohol-containing potable comprises edible alcohol; and the at least one organic acid comprises acetic acid, lactic acid, butanedioic acid, hexanoic acid, and tartaric acid in a weight ratio of 3:3:1:1:2, and wherein the at least one physiological process is at least one member selected from the group consisting of regulating sexual functions, protecting cardiovascular and cerebrovascular systems, promoting regeneration of liver cells, preventing tumors, treating tumors, improving immunity, and improving sleep quality.

2. A composition comprising:

at least one alcohol-containing potable;

at least one cooling agent; and at least one organic acid, wherein the composition is selected from the group consisting of (1) Composition 1 comprising 1% alcohol by volume, 0.05 ppm of the at least one cooling agent, 150 ppm of the at least one organic acid, and water, wherein:

the at least one cooling agent comprises menthyl acetate, L-menthyl lactate, and monomethyl succinate in a weight ratio of 4:5:1;

the at least one alcohol-containing potable comprises beer; and the at least one organic acid comprises acetic acid, lactic acid, propionic acid, butyric acid, and hexanoic acid in a weight ratio of 14:15:1.5:1:1;

(2) Composition 2 comprising 30% alcohol by volume, 10 ppm of the at least one cooling agent, 1000 ppm of the at least one organic acid, and water, wherein:

the at least one cooling agent comprises monomethyl succinate, L-monomenthyl glutarate, and N-ethyl-2-isopropyl-5-methylcyclohexane carboxamide in a weight ratio of 2:5:3;

the at least one alcohol-containing potable comprises whiskey; and the at least one organic acid comprises acetic acid, lactic acid, propionic acid, butanedioic acid, pentanoic acid, and heptanoic acid in a weight ratio of 7:8:1:2:1:1;

(3) Composition 3 comprising 60% alcohol by volume, 100 ppm of the at least one cooling agent, 6000 ppm of the at least one organic acid, and water, wherein:

the at least one cooling agent comprises N,2,3-trimethyl-2-isopropylbutamide, L-menthyl lactate, monomethyl succinate, and L-menthol ethylene glycol carbonate in a weight ratio of 2:3:2:3;

the at least one alcohol-containing potable comprises Baijiu; and the at least one organic acid comprises formic acid, acetic acid, lactic acid, propionic acid, octanoic acid, nonanoic acid, and decanoic acid in a weight ratio of 1:8:5:2:1:1:1;

(4) Composition 4 comprising 80% alcohol by volume, 200 ppm of the at least one cooling agent, 10,000 ppm of the at least one organic acid, and water, wherein:

the at least one cooling agent comprises monomethyl succinate, L-monomenthyl glutarate, and N-ethyl-2-isopropyl-5-methylcyclohexane carboxamide in a weight ratio of 3:4:3;

the at least one alcohol-containing potable comprises rice liquor and edible alcohol; and the at least one organic acid comprises acetic acid, lactic acid, propionic acid, citric acid, malic acid, and tartaric acid in a weight ratio of 5:5:1:2:1:1;

(5) Composition 5 comprising 99% alcohol by volume, 500 ppm of the at least one cooling agent, 30,000 ppm of the at least one organic acid, and water, wherein:

the at least one cooling agent comprises N,2,3-trimethyl-2-isopropylbutamide, L-menthyl lactate, 3-L-menthoxypropane-1,2-diol, L-menthol propylene glycol carbonate, and L-monomenthyl glutarate in a weight ratio of 4:1:2:3:1;

the at least one alcohol-containing potable comprises dehydrated ethanol; and the at least one organic acid comprises lactic acid, propionic acid, hexanoic acid, citric acid, and malic acid in a weight ratio of 5:1:1:2:2;

(6) Composition 6 comprising 50% alcohol by volume, 50 ppm of the at least one cooling agent, 3000 ppm of the at least one organic acid, and water, wherein:

the at least one cooling agent comprises menthyl acetate, L-menthyl lactate, and N,2,3-trimethyl-2-isopropylbutamide in a weight ratio of 2:3:5;

the at least one alcohol-containing potable comprises Baijiu; and the at least one organic acid comprises acetic acid, butanedioic acid, hexanoic acid, citric acid, and malic acid in a weight ratio of 3:1:1:4:2; and (7) Composition 7 comprising 70% alcohol by volume, 150 ppm of the at least one cooling agent, 8000 ppm of the at least one organic acid, and water, wherein:

the at least one cooling agent comprises L-menthyl lactate and monomethyl succinate in a weight ratio of 4:6;

the at least one alcohol-containing potable comprises edible alcohol; and the at least one organic acid comprises acetic acid, lactic acid, butanedioic acid, hexanoic acid, and tartaric acid in a weight ratio of 3:3:1:1:2;

and wherein the composition is effective for regulating at least one physiological process selected from the group consisting of regulating sexual functions, protecting cardiovascular and cerebrovascular systems, promoting regeneration of liver cells, preventing tumors, treating tumors, improving immunity, and improving sleep quality of an individual to whom the composition is administered.

3. The composition of claim 2, consisting of the Composition 1.

4. The composition of claim 2, consisting of the Composition 2.

5. The composition of claim 2, consisting of the Composition 3.

6. The composition of claim 2, consisting of the Composition 4.

7. The composition of claim 2, consisting of the Composition 5.

8. The composition of claim 2, consisting of the Composition 6.

9. The composition of claim 2, consisting of the Composition 7.

10. The method of claim 1, wherein the at least one composition comprises the Composition 1.

11. The method of claim 1, wherein the at least one composition comprises the Composition 2.

12. The method of claim 1, wherein the at least one composition comprises the Composition 3.

13. The method of claim 1, wherein the at least one composition comprises the Composition 4.

14. The method of claim 1, wherein the at least one composition comprises the Composition 5.

15. The method of claim 1, wherein the at least one composition comprises the Composition 6.

16. The method of claim 1, wherein the at least one composition comprises the Composition 7.

17. The method of claim 1, wherein sexual functions of the individual are regulated by the administering of the at least one composition to the individual.

18. The method of claim 1, wherein the cardiovascular and cerebrovascular systems of the individual are protected by increased nitric oxide levels in the individual induced by the administering of the at least one composition to the individual.

19. The method of claim 1, wherein the regeneration of liver cells of the individual is promoted by the administering of the at least one composition to the individual.

20. The method of claim 1, wherein the administering of the at least one composition to the individual inhibits tumor development in the individual.

21. The method of claim 1, wherein the administering of the at least one composition to the individual improves the immunity of the individual.

22. The method of claim 1, wherein the administering of the at least one composition to the individual improves the sleep quality of the individual.

* * * * *